(12) United States Patent
Connor et al.

(10) Patent No.: US 9,279,142 B2
(45) Date of Patent: Mar. 8, 2016

(54) DEVICE AND METHOD OF TAKING SAMPLES FROM MEDICAL EQUIPMENT FOR THE PURPOSE OF MICROBIOLOGICAL TESTING

(75) Inventors: Guy Connor, Hornsby (AU); Roland Ian Stokes, Hornsby (AU); David Frank, Hornsby (AU)

(73) Assignee: ENDOWORX PTY LTD, Hornsby, New South (AU)

( * ) Notice: Subject to any disclaimer, the term of this patent is extended or adjusted under 35 U.S.C. 154(b) by 370 days.

(21) Appl. No.: 13/977,741

(22) PCT Filed: Jan. 11, 2012

(86) PCT No.: PCT/AU2012/000013
§ 371 (c)(1),
(2), (4) Date: Jul. 31, 2013

(87) PCT Pub. No.: WO2012/094702
PCT Pub. Date: Jul. 19, 2012

(65) Prior Publication Data
US 2013/0302848 A1    Nov. 14, 2013

(30) Foreign Application Priority Data
Jan. 12, 2011 (AU) ................. 2011900078

(51) Int. Cl.
G01N 1/14 (2006.01)
C12Q 1/24 (2006.01)
A61B 1/00 (2006.01)
A61B 1/12 (2006.01)

(52) U.S. Cl.
CPC .............. *C12Q 1/24* (2013.01); *A61B 1/00057* (2013.01); *A61B 1/125* (2013.01)

(58) Field of Classification Search
None
See application file for complete search history.

(56) References Cited

U.S. PATENT DOCUMENTS

| 4,707,450 | A | | 11/1987 | Nason |
| 4,930,360 | A | | 6/1990 | Tan |
| 5,632,717 | A | * | 5/1997 | Yoon ............................ 600/106 |
| 5,795,404 | A | | 8/1998 | Murphy et al. |
| 2003/0004474 | A1 | | 1/2003 | Barker |
| 2006/0039833 | A1 | | 2/2006 | Yong |
| 2008/0045859 | A1 | * | 2/2008 | Fritsch et al. ................. 600/567 |
| 2010/0136670 | A1 | * | 6/2010 | Markovsky ................ 435/288.1 |

OTHER PUBLICATIONS

International Search Report Corresponding to PCT/AU2012/000013 mailed Mar. 21, 2012.
International Preliminary Examination Report Corresponding to PCT/AU2012/000013 mailed Jul. 17, 2012.

* cited by examiner

*Primary Examiner* — Robert R Raevis
(74) *Attorney, Agent, or Firm* — Davis & Bujold PLLC; Michael J. Bujold (57) ABSTRACT

A device and method for use in taking a sample from an item of medical equipment for the purpose of microbiological testing. The device includes attachment mechanism for attaching about a region of the item of medical equipment in an air-tight manner; and collection mechanism for collecting fluid which emanates from the item of medical equipment.

10 Claims, 9 Drawing Sheets

Fig 1

PRIOR ART

Sect. A-A

Sect. B-B

Fig 9

DEVICE AND METHOD OF TAKING SAMPLES FROM MEDICAL EQUIPMENT FOR THE PURPOSE OF MICROBIOLOGICAL TESTING

This application is a National Stage completion of PCT/AU2012/000013 filed Jan. 11, 2012, which claims priority from Australian patent application serial no. 2011900078 filed Jan. 12, 2011.

TECHNICAL FIELD

The present invention relates to devices for, and methods of, taking samples from medical equipment for the purpose of microbiological testing. The invention has particular application to taking samples from endoscopes and dialysis machines but is not limited to those uses.

BACKGROUND TO THE INVENTION

An endoscope is an instrument used to examine the interior of a hollow organ or cavity of the body. They are most typically used to make inspections of the gastrointestinal tract, or the respiratory tract.

Following each use on a patient, the endoscope must be cleaned and reprocessed to achieve the recommended standard of sterilization or high level disinfection to reduce the risk of cross-infection of subsequent patients. Following reprocessing the scopes are to be stored in a manner applicable to the standard of sterilization or high level disinfection, the endoscope is wrapped in a protective wrapper or stored in a suitable scope cabinet ready for the next use.

In order to ensure that endoscopes are being properly sterilized, a microbiological surveillance regimen is typically adhered to. This involves routine testing of endoscopes at fixed time intervals, such as every 4 to 12 weeks. The endoscopes are tested by obtaining a sample from the endoscope channels, the sample is then cultured and analyzed for the presence of bacteria.

The sample is usually obtained using sterile water, a sterile container, and an endoscope brush in the following manner:
  Sterile water is flushed into each of the channels to be brushed, and any water which emerges from the distal tip is collected.
  The brush is inserted into the biopsy channel of the endoscope, withdrawn and swirled in the water in the sterile container
  Remaining brushable channels such as the suction channel of the endoscope are brushed and brush swirled in collection device again.
  Using a sterile syringe, sterile water is flushed under positive pressure through each of the channels in turn. Flushing is performed from the connection points in the light guide plug and flow to the distal tip. Fluid is flushed until it emerges from the tip.
  Air is then syringed through to empty the remaining fluid from each of the channels. The total rinse fluid is collected in the sterile container.
  The container is sealed, labeled, and sent for testing.

Throughout the sampling procedure, attention must be paid to preventing the tip of the endoscope from touching the container so as to avoid contamination. Furthermore, the body of the endoscope must be kept in a raised position with respect to its distal end to ensure that fluid flows in the intended direction, towards and out of the distal end. This means that the sampling procedure must be carried out by a team of two people. One person stands at a raised position, such as by standing on a chair, and introduces the sterile water. The second person holds the distal end of the endoscope at the mouth of the sterile container to collect water emanating from the tip of the endoscope.

Furthermore, the mouth of the sterile container is open to the air during the sampling procedure, which gives rise to a risk of false positive test results, which in turn necessitate a repeated and unnecessary test of the same endoscope.

Similar issues are experienced in sampling procedures carried out other types of medical equipment, such as dialysis machines.

There remains a need for improvements in procedures for obtaining samples from medical equipment.

SUMMARY OF THE INVENTION

In a first aspect the present invention provides a device for use in taking a sample from an item of medical equipment for the purpose of microbiological testing including: attachment means for attaching about a region of the item of medical equipment in an air-tight manner; and collection means for collecting fluid which emanates from the item of medical equipment.

The device may further include a suction means for sucking air from the collection means, to thereby draw fluid from the item of medical equipment.

The suction means may be provided in the form of a cylinder and plunger arrangement.

The cylinder and plunger may be embodied in a sterile syringe.

The suction means may include a pair of one way valves which allow for reciprocation of the cylinder and plunger arrangement.

The device may further include an aperture for allowing the introduction of a brush in to the collection means.

The attachment means may include a resilient portion which forms an air-tight seal with the item of medical equipment.

The attachment means may further include prongs which space the item of medical equipment away from internal surfaces of the device.

In a second aspect the present invention provides a method of collecting a sample from an item of medical equipment for the purpose of microbiological testing including the steps of: attaching a reservoir of sterile fluid to one end of a channel of the item of medical equipment; attaching a collecting means about the second end of the channel in an air-tight manner; passing fluid through the channel of the item of medical equipment; and collecting fluid which emanates from the channel.

The fluid may be caused to pass through the channel by way of withdrawing air from the collection means.

The air may be withdrawn manually by way of a cylinder and plunger arrangement.

The cylinder and plunger arrangement may be provided in the form of a syringe.

The method may further include the step of brushing the channel.

The method may further include the step of placing a portion of the brush into the collection means and sealing the collection means with the portion of the brush inside.

BRIEF DESCRIPTION OF THE DRAWINGS

An embodiment of the present invention will now be described, by way of example only, with reference to the accompanying drawings, in which.

DETAILED DESCRIPTION OF THE PREFERRED EMBODIMENT

Embodiments of the invention will now be described with reference to taking samples from an endoscope.

Figure 1:
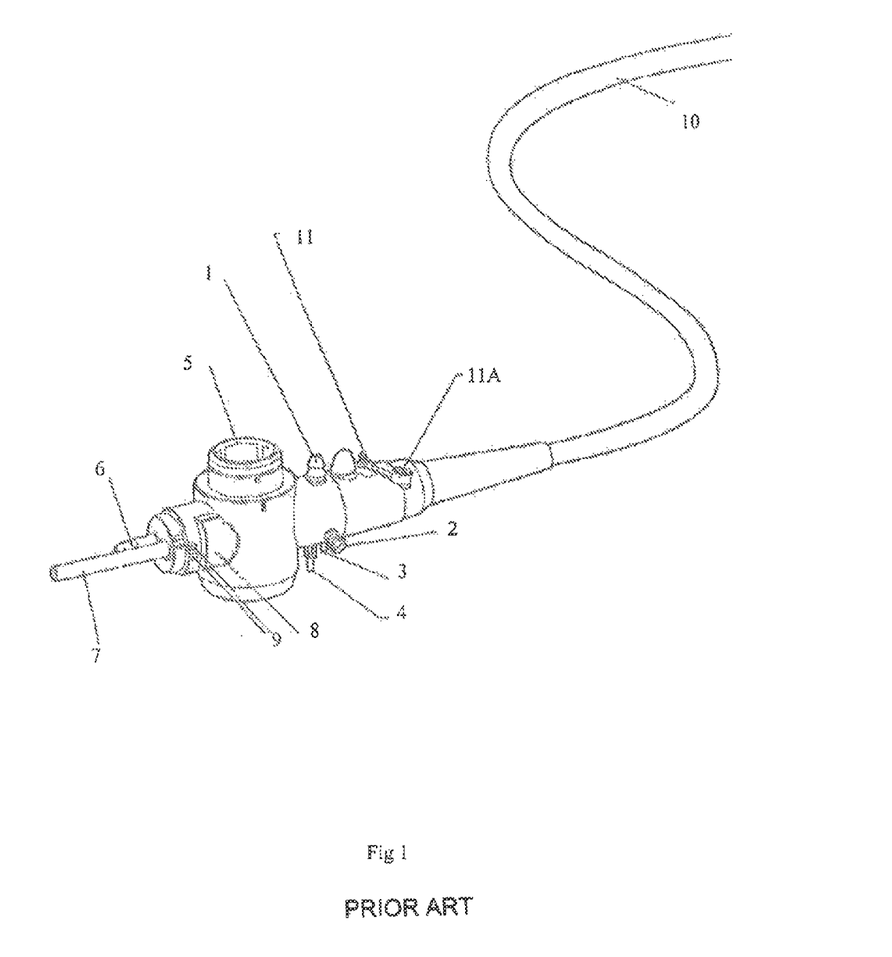
FIG. 1 is a perspective view of the connector section of a typical endoscope.
Figure 2:
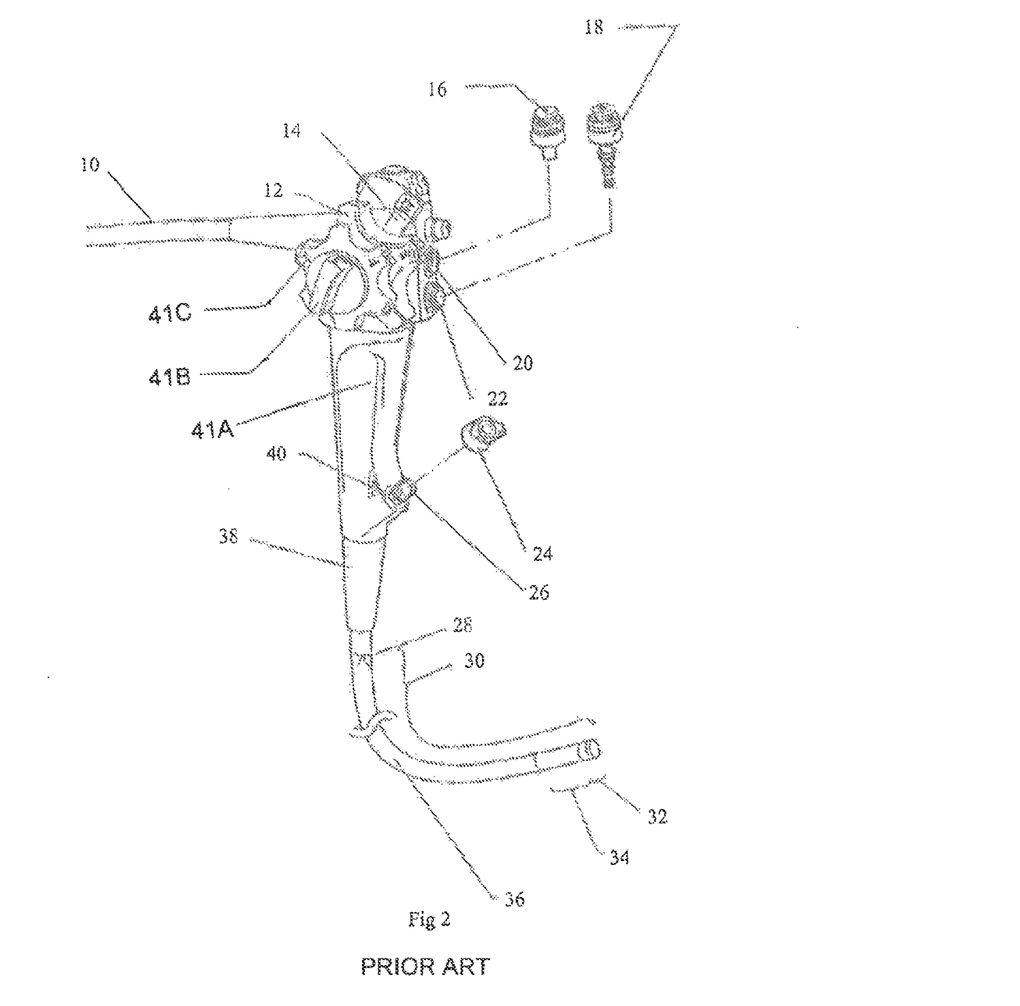
FIG. 2 is a perspective view of the control section of the endoscope of FIG. 1.
Figure 3:
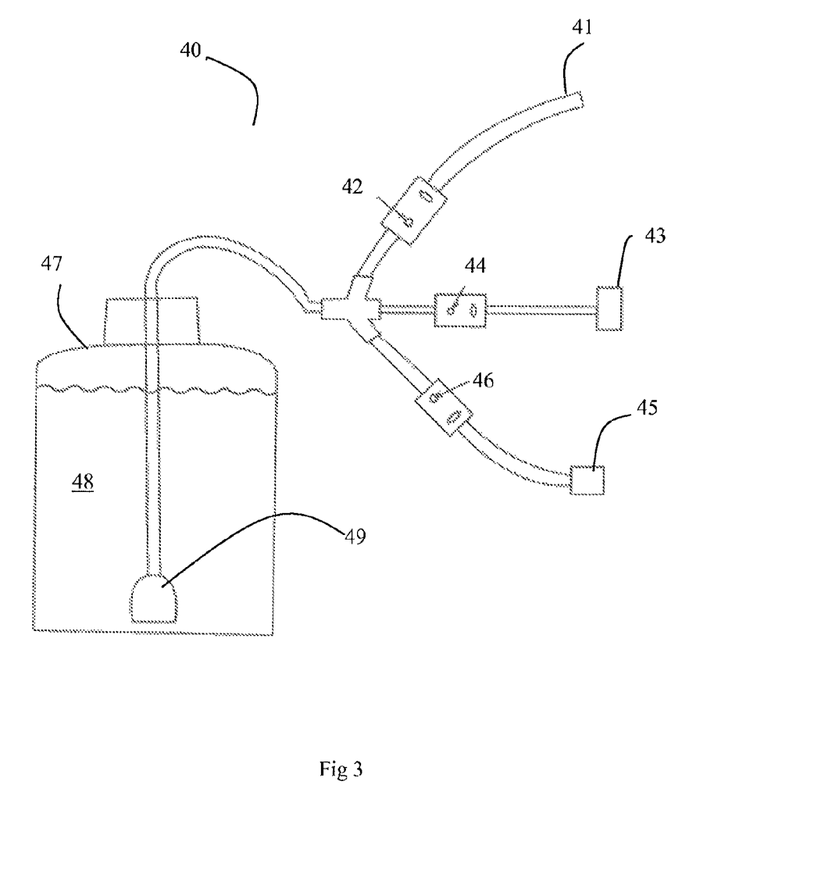
FIG. 3 shows apparatus according to an embodiment of the present invention.

Referring to FIGS. 1 and 2, an endoscope of typical construction is shown comprised of a connector section (see FIG. 1) and a control section (see FIG. 2) which are joined by a universal cord 10. The working length 30 is shown of truncated length in FIG. 2 for ease of illustration. Endoscope comprises the following usual features labeled by number as follows:

1. Suction connector
2. S-cord connector mount
3. Air supply connector
4. Water supply connector
5. Electrical connector
6. Air pipe
7. Light guide
8. Product name and serial number
9. Electrical contacts
10. Universal cord
11. Auxiliary water inlet
11A. Auxiliary water inlet cap
12. UP/DOWN angulation control knob
14. UP/DOWN angulation lock
16. Suction valve
18. Air/water valve
20. Suction cylinder
22. Air/water cylinder
24. Biopsy valve
26. Instrument channel port
28. Insertion tube limit mark
30. Working length
32. Distal end
34. Bending section
36. Insertion tube
38. Boot
40. Color code
41A Grip section
41B RIGHT/LEFT angulation lock
41C RIGHT/LEFT angulation control knob Referring to FIGS. 3 and 4, apparatus is shown for use in taking samples from an endoscope such as the one shown in FIGS. 1 and 2. Referring to FIG. 3, a sterile water supply arrangement 40 is shown including a branched tubular arrangement with suction channel connection 41, air/water connection 43 and auxiliary water channel connection 45, each with associated stopcocks 42, 44 and 46 for controlling the flow of water through each of the pipe branches. Jar 47 holds a supply of sterile water 48 which is drawn from jar 47 by way of downpipe 49.

Figure 4:
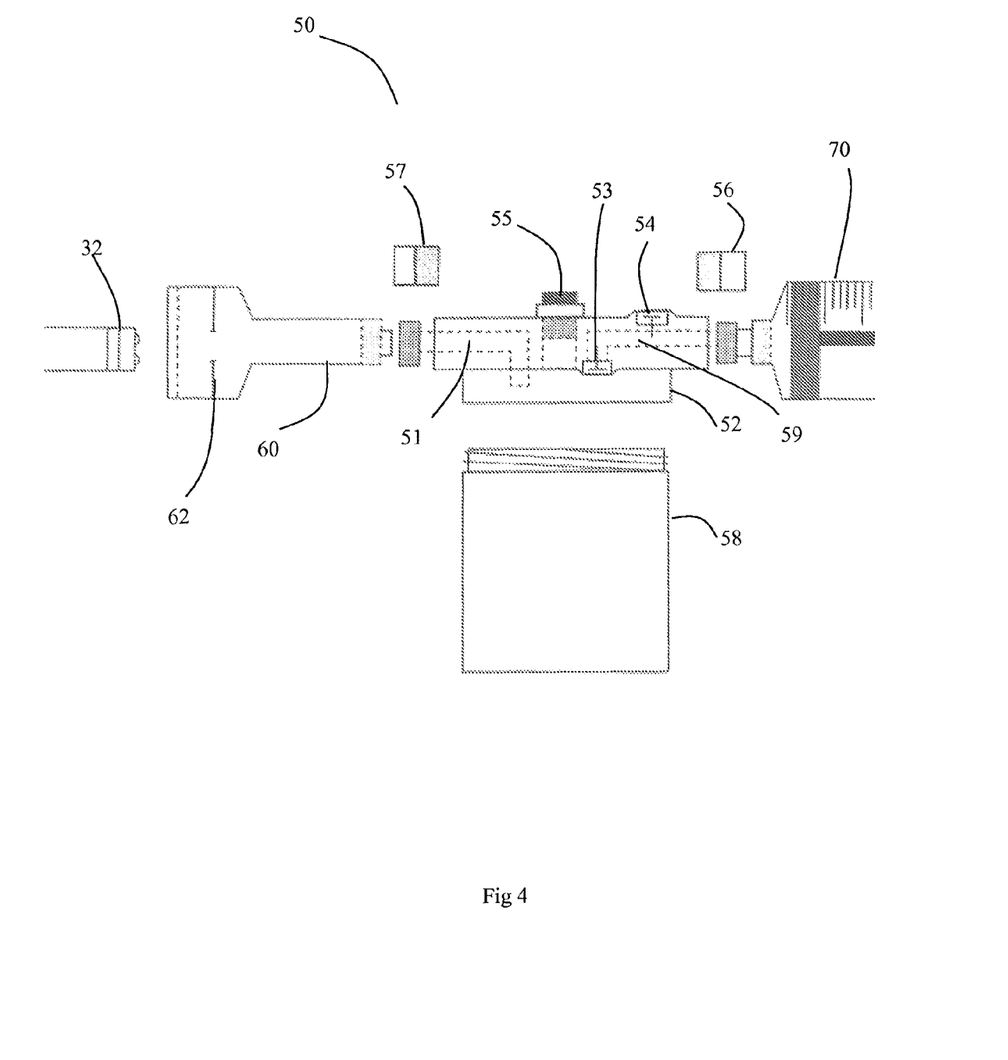
FIG. 4 shows additional apparatus according to an embodiment the present invention.

Referring to FIG. 4, a device 50 for use in taking samples from endoscopes is shown including attachment means in the form of insertion attachment 60 for attaching in an air-tight manner to distal end 32 of the endoscope by way of interference fit of the distal end 32 into membrane 62 which is provided with a central aperture. Device 50 further includes collection means in the form of sample container 58 and lid assembly 52. A suction means in the form of a piston and cylinder arrangement is provided by sterile syringe 70. Protective caps (shown in removed position) 57, 56 are used to seal channels 51, 59 which are provided in lid assembly 52. Insertion attachment 60 fits to one end of channel 51, syringe 70 fits to one end of channel 59. The other ends of the channels open at the underside of lid assembly 52. Channel 59 is fitted with two one-way valves 53, 54. Valve 53 permits flow of air in the direction out of sample container 58, but prevents flow of air into the sample container. Similarly, valve 54 permits air to flow in a direction out to the atmosphere, but prevents ingress of air into channel 59 from the atmosphere. When the plunger of syringe 70 is reciprocated back and forth, then the valve arrangement gives rise to a partial vacuum inside sample container 58. This partial vacuum acts to draw sterile water from the jar 47, through one of the channels of the endoscope, and into sample container 58 as will be later described.

Brush aperture seal 55 allows an item, such as the tip of a brush, to be introduced into container 58 by removing and replacing the seal 55.

In order to take a sample from an endoscope, the following steps are carried out:

1. Lay the endoscope on a bench or other surface.
2. Attach suction channel connection 41 to suction connector 1.
3. Attach air/water connection 43 to air pipe 6
2. Attach suction channel connection 41 to suction connector 1.
4. Attach auxiliary water channel connector 45 to auxiliary water inlet 11
5. Put in place an air/water bridge connecting air supply connector 3 with water supply connector 4. Put in place suction valve 16, air/water valve 18, and biopsy valve 24
6. Ensure that all of stopcocks 42, 44 and 46 are in their closed positions.
7. Fit insertion attachment 60 and syringe 70 to lid assembly 52 and fit sample container 58. Push fit distal end 32 of endoscope into insertion attachment 62,
8. Open stop cock 42. Reciprocate the plunger of syringe 70 to draw sterile water through the biopsy channel. Continue until approx 10 ml to 100 ml of water has emanated from distal tip 32 to be collected in container 58. Close stop cock 42.
9. Open stop cock 44. Reciprocate the plunger of syringe 70 to draw sterile water through the air/water channel. Continue until approx 10 ml of water has emanated from distal tip 32 to be collected in container 58. Close stop cock 44.
10. Open stop cock 46. Reciprocate the plunger of syringe 70 to draw sterile water through the auxiliary water channel. Continue until approx 10 ml of water has emanated from distal tip 32 to be collected in container 58. Close stop cock 46.
11. Remove insertion attachment 60 and syringe 70 from lid assembly. Re-seal channels 51, 59 with caps 57, 56, 12. Remove all channel blockers and accessories from the endoscope. Using the disposable sterile brush supplied, brush the biopsy and the suction channels.

13. Collect the brush sample by removing seal 55, insert the tip of brush into the sample container 58 and cut off the tip of the brush to leave the tip of the brush inside container 58. Replace seal 55.

14. Label sample container 58 and send away for testing.

Referring to FIGS. 5 to 9, an alternative embodiment of apparatus is shown which operates along the same principles as the embodiment described above, but has various structural differences. Like reference numerals have been used to indicate with like functions to the first described embodiment.

Device 150 includes an insertion attachment 160, a sample container 158 and a lid assembly 152. Lid assembly 152 clips to sample container 158 in an airtight manner.

Figure 8:
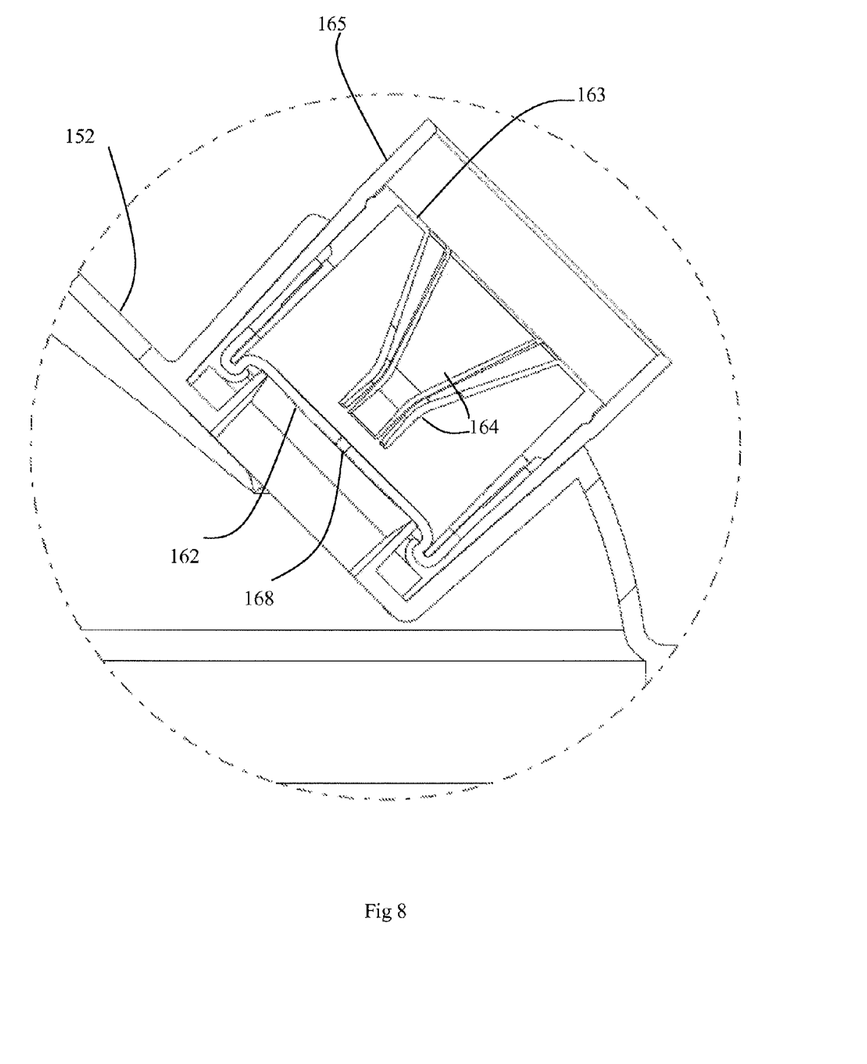
FIG. 8 is an enlarged view of detail A of FIG. 7.
Figure 9:
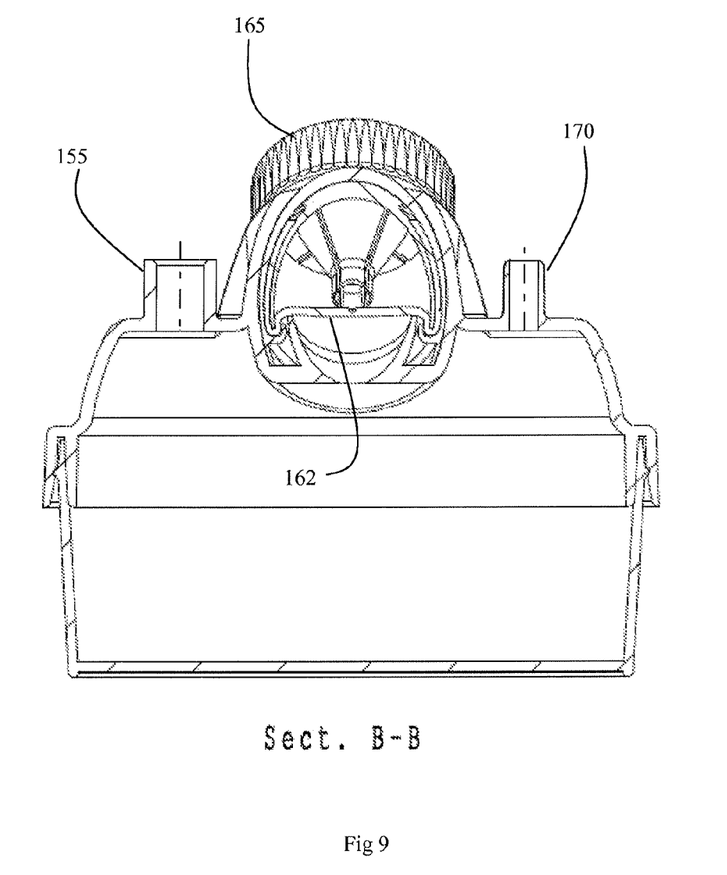
FIG. 9 is a cross-sectional view along the line B-B of FIG. 6.

The insertion attachment 160 is best seen at FIG. 8 and is formed from three components being plug 165, a circular silicone membrane 162 and insert 163. Insert 163 is a snap fit inside plug 165 and the membrane is retained about its periphery by being trapped between plug 165 and insert 163. The insertion attachment 160 is a push fit into lid assembly 152. Membrane includes a central aperture 168. When a region of an item of medical equipment, such as the end of an endoscope, is inserted into insertion attachment 160 and through aperture 168, the silicone membrane expands to fit about the medical equipment to form an air-tight seal. An arrangement of four prongs 164 serves to support the medical equipment that is inserted and to space it away from the inside surfaces of the device 150 to prevent contamination of the sample. Alternative inserts having more closely spaced, or widely spaced prongs, may be provided to accommodate items of medical equipment of various sizes.

Figure 5:
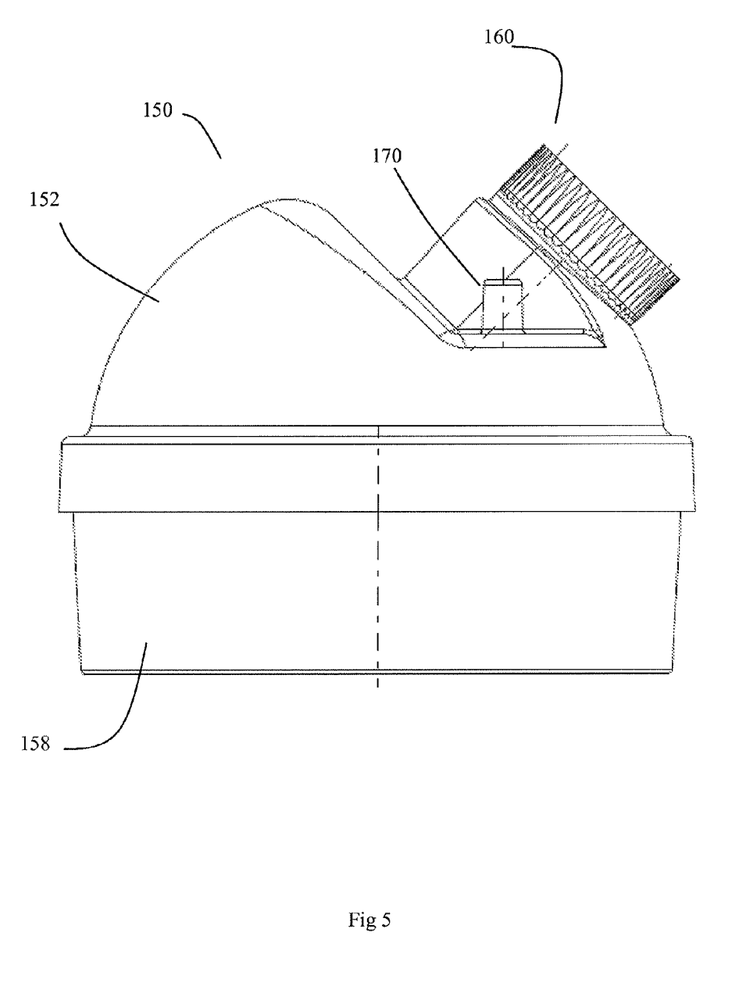
FIG. 5 is a side view of apparatus according to alternative embodiment of the invention.

The device 150 supports the end of the item of medical equipment introduced into it at an angle of approximately 45 degrees to the surface upon which device 150 is resting.

Figure 6:
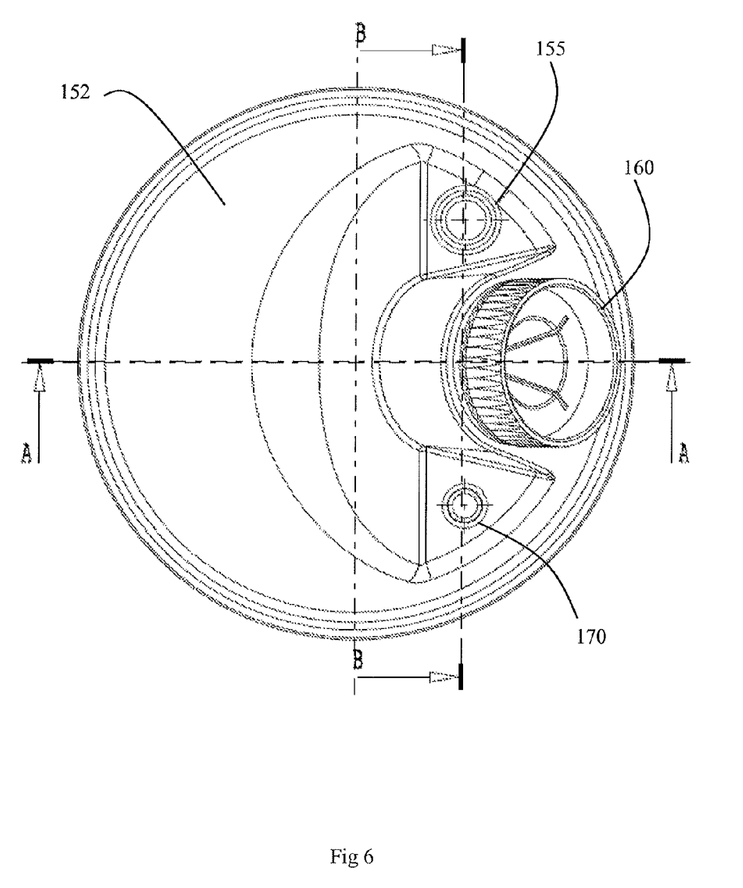
FIG. 6 is a top view of the apparatus of FIG. 5.
Figure 7:
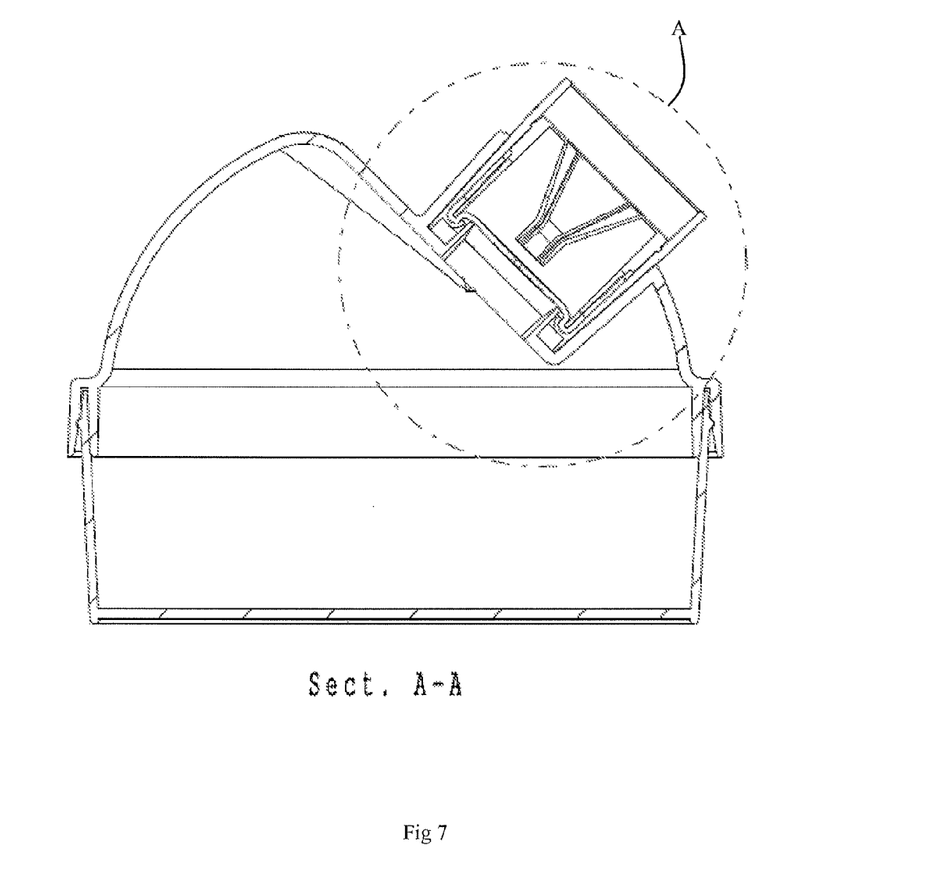
FIG. 7 is a cross-sectional view along the line A-A of FIG. 6.

An air withdrawal port 170 is provided on lid assembly 152 to which is fitted a tube which connects to a suction device, such as one similar to the syringe and double-valve arrangement described in the first embodiment. By withdrawing air from port 170, a partial vacuum is created inside device 150 which serves to draw fluid through a channel in the medical equipment.

Another sealable port 155 is provided so that the tip of a brush may be introduced into device 150 in a similar fashion as that described above.

Except for the silicone membrane, all parts of device 150 are formed from ABS plastic.

When the sampling procedure is complete, the insertion attachment 160 is removed and replaced by a stopper. The device 150 containing the sample is then ready to be sent away to a laboratory for microbial testing.

It can be seen that embodiments of the invention have at least one of the following advantages:

The procedure of taking a sample from the endoscope can be carried out by one person.

The procedure for taking a sample from the endoscope may be carried out with the endoscope laid out on a worktop. There is no need to maintain the body of the endoscope at a raised height.

The sample collecting container is sealed from the atmosphere during sample collection, thereby reducing risk of false positive readings due to airborne contaminants.

The sample is drawn by manual operation of a syringe, thus allowing accurate control over the sampling procedure.

Procedure involves destruction of a disposable brush, thus reducing false positives arising from reuse of brushes.

A sterile brush is supplied with each collection kit to further reduce the risk of false positive test results.

Whilst the embodiments above were described with reference to taking samples from an endoscope, they could similarly be used with other items of medical equipment which have channels through which fluid may be passed such as dialysis machines and the like.

Whilst the embodiment described above utilized a syringe to provide suction, in other embodiments an electrically powered suction pump could be used instead.

Any reference to prior art contained herein is not to be taken as an admission that the information is common general knowledge, unless otherwise indicated.

Finally, it is to be appreciated that various alterations or additions may be made to the parts previously described without departing from the spirit or ambit of the present invention.

The invention claimed is:

1. A device for use in taking a sample from an item of medical equipment for the purpose of microbiological testing, the device comprising:
   attachment means for attaching about a region of the item of medical equipment in an air-tight manner;
   collection means for collecting fluid which emanates from the item of medical equipment;
   the collection means including a sample container and a lid assembly, and the lid assembly coupling the sample container to the attachment means; and
   the attachment means including a resilient portion in the form of a membrane which includes an aperture, and the membrane forming an air-tight seal by way of being an interference fit about the region of the item of medical equipment.

2. The device according to claim 1, further including a suction means for sucking air from the collection means to thereby draw fluid from the item of medical equipment.

3. The device according to claim 2, wherein the suction means is provided in the form of a cylinder and plunger arrangement.

4. The device according to claim 3, wherein the cylinder and plunger are embodied in a sterile syringe.

5. The device according to claim 3, wherein the suction means includes a pair of one way valves which allow for reciprocation of the cylinder and plunger arrangement.

6. The device according to claim 1, wherein the lid assembly further including an aperture for allowing introduction of a brush into the collection means.

7. The device according to claim 1, wherein the attachment means further includes prongs which space the item of medical equipment away from internal surfaces of the device.

8. A method of collecting a sample from an item of medical equipment for the purpose of microbiological testing, the method comprising the steps of:
   attaching a reservoir of sterile fluid to one end of a channel of the item of medical equipment;
   attaching a device about the second end of the channel in an air-tight manner, the device comprising attachment means for attaching about a region of the item of medical equipment in an air-tight manner; collection means for collecting fluid which emanates from the item of medical equipment; and the attachment means including a resilient membrane which includes an aperture, and the membrane forming an air-tight seal by way of an interference fit about the region of the item of medical equipment;
   passing fluid through the channel of the item of medical equipment; and
   collecting fluid which emanates from the channel.

9. The method according to claim 8, further comprising the step of brushing the channel.

10. The method according to claim 9, further comprising the step of placing a portion of the brush into the collection means of the device and sealing the collection means with the portion of the brush inside.

\* \* \* \* \*